United States Patent [19]

Lalinde et al.

[11] Patent Number: 4,994,471

[45] Date of Patent: Feb. 19, 1991

[54] N-ARYL-N-(1-SUBSTITUTED-3-ALKOXY-4-PIPERIDINYL)AMIDES AND PHARMACEUTICAL COMPOSITIONS AND METHODS EMPLOYING SUCH COMPOUNDS

[75] Inventors: Nhora L. Lalinde, West Nyack; John Moliterni, Staten Island, both of N.Y.; H. Kenneth Spencer, Chatham, N.J.

[73] Assignee: BOC, Inc., New Providence, N.J.

[21] Appl. No.: 351,360

[22] Filed: May 12, 1989

[51] Int. Cl.$^5$ .................. A61K 31/445; C07D 333/06
[52] U.S. Cl. .................................... 514/326; 546/209; 546/213
[58] Field of Search ................. 546/209, 213; 514/326

[56] References Cited

U.S. PATENT DOCUMENTS

| | | | |
|---|---|---|---|
| 3,164,600 | 1/1965 | Janssen | 546/213 |
| 3,998,834 | 12/1976 | Janssen et al. | 546/213 |
| 4,138,492 | 2/1979 | Noverola et al. | 514/316 |
| 4,167,574 | 9/1979 | Janssen | 514/326 |
| 4,584,303 | 4/1986 | Huang et al. | 514/326 |
| 4,810,791 | 3/1989 | Weller et al. | 546/210 X |

OTHER PUBLICATIONS

G. Van Daele et al., *Drug Development Research*, vol. 8, (1986), pp. 225–232.

P. A. Olofson et al., *J. Org. Chem.*, vol. 49, (1984), pp. 2081–2082.

P. Van Daele et al., *Arzneim–Forsch. Drug Res.*, vol. 26, (1976), pp. 1521–1531.

A. H. Becket et al., *J. Med. Pharm. Chem.*, vol. 1, (1959), pp. 37–59.

C. R. Ganellin et al., *J. Med. Chem.*, vol. 8, (1965), pp. 619–625.

P. M. Carabateas et al., *J. Med. Pharm. Chem.*, vol. 5, (1962), pp. 913–919.

Moriarty et al., *Tetrahedron Letters*, vol. 25, No. 42, (1984), pp. 4745–4748.

Y. Zhu et al., *Acta Pharm. Sinica*, vol. XVI, No. 3, (1981), pp. 199–210.

*Chem. Abstr.*, 82, 156121u (1975), [OLS 2,341,965, 3/6/75].

*Primary Examiner*—Alan L. Rotman
*Assistant Examiner*—Jacqueline Haley
*Attorney, Agent, or Firm*—R. Hain Swope; Larry R. Cassett

[57] ABSTRACT

This invention pertains to novel N-aryl-N-[N-substituted 3-alkoxy-4-piperidinyl]amides useful as analgesics, and methods of administering analgesia, which comprises the systemic administration to mammals of such compounds, and pharmaceutical compositions containing such compounds, wherein the novel compounds have the general formula:

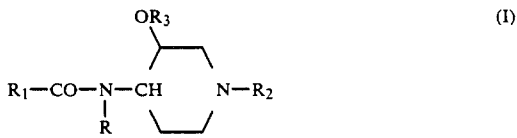

including optically active isomeric forms, cis/trans isomeric forms and the pharmaceutically acceptable acid addition salts therof, wherein:

R is an aryl group selected from the group consisting of phenyl and substituted phenyl, wherein the substituents on the phenyl group are independently selected from the group consisting of halogen, lower-alkyl, lower-alkoxy, and combinations thereof;

$R_1$ is an alkyl group selected from the group consisting of lower-alkyl, lower-alkenyl, and lower-alkoxy lower-alkyl, each alkyl group having from 1 to 6 carbon atoms;

$R_2$ is a member selected from the group consisting of phenyl lower-alkyl, thienyl lower-alkyl, pyrazolyl lower-alkyl, tetrazolyl lower-alkyl, 4,5-dihydro-5-oxo-1H-tetrazolyl lower-alkyl, 1,3-dihydro-1,3-dioxo-2H-isoindolyl lower-alkyl, and 2,3-dihydro-2-oxo-1H-benzimidazolyl lower-alkyl; and $R_3$ is a member selected from the group consisting of hydrogen, lower-alkyl and lower-alkyl aryl.

21 Claims, No Drawings

N-ARYL-N-(1-SUBSTITUTED-3-ALKOXY-4-PIPERIDINYL)AMIDES AND PHARMACEUTICAL COMPOSITIONS AND METHODS EMPLOYING SUCH COMPOUNDS

The present invention relates to N-aryl-N-[1-substituted-3-alkoxy-4-piperidinyl]amides and pharmaceutical compositions and methods employing such compounds. In particular, this new class of compounds possesses potent analgesic and anesthetic properties.

BACKGROUND OF THE INVENTION

A number of patents disclose certain N-aryl-N-(1-substituted-4-piperidinyl)amides having analgesic activity. For example, U.S. Pat. Nos. 3,998,834, 3,164,600, and 4,167,574, issued to Janssen et al. and assigned to Janssen Pharmaceuticals N.V., disclose certain N-phenyl-N-[1-(aryl -substituted)-4-piperidinyl]amide compounds, N-aryl-N-[1-(arylalkyl)-4-piperidinyl] amides and N-aryl-N-[1-(tetrazolyl-substituted)-4-piperidinyl]amides useful as analgesics. U.S. Pat. No. 4,584,303, issued to Huang et al. and assigned to The BOC Group, Inc., discloses certain N-phenyl-N-[1-(heterocyclic)-4-piperidinyl]amide compounds useful as analgesics.

U.S. Pat. No. 4,138,492, issued to Noverola et al. and assigned to Anphar, S. A., discloses certain N-[4'(1'-arylalkyl)piperidinyl]-4-amiino-5-halo-2-alkoxy benzamide compounds. Van Daele et al., *Drug Development Research*, 8, 225–232 (1986), discloses the preparation of certain 3-hydroxy-4,4-dimethoxy-1-phenylmethyl piperidine derivatives.

SUMMARY OF THE INVENTION

This invention pertain to novel N-aryl-N-[1-substituted-3-alkoxy-4-piperidinyl]amides useful as analgesics, and methods of administering analgesia, which comprises the systemic administration to mammals of such compounds, and pharmaceutical compositions containing such compounds, wherein the novel compounds have the general formula:

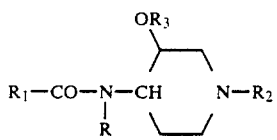

including optically active isomeric forms, cis/trans isomeric forms and the pharmaceutically acceptable acid addition salts thereof, wherein:

R is an aryl group selected from the group consisting of phenyl and substituted phenyl, wherein the substituents on the phenyl group are independently selected from the group consisting of halogen, lower-alkyl lower alkoxy, and combinations thereof;

$R_1$ is an alkyl group selected from the group consisting of lower-alkyl, lower-alkenyl, and lower-alkoxy lower-alkyl, each alkyl group having from 1 to 6 carbon atoms;

$R_2$ is a member selected from the group consisting of phenyl lower-alkyl, thienyl lower-alkyl, pyrazolyl lower-alkyl, tetrazolyl lower-alkyl, 4,5-dihydro-4-oxo-1H-tetrazolyl lower-alkyl, 1,3-dihydro-1,3-dioxo-2H-isoindolyl (N-phthalimidyl) lower-alkyl, and 2,3-dihydro-2-oxo-1H-benzimidazolyl lower-alkyl; and $R_3$ is a member selected from the group consisting of hydrogen, lower-alkyl and lower-alkyl aryl.

DETAILED DESCRIPTION OF THE INVENTION

The compounds of the present invention possess very desirable analgesic activities. In particular, the inventive compounds have central nervous system depressant properties which include analgesia, hypnosis, sedation, muscle relaxation, increased pain threshold, and barbiturate and/or general anesthetic potentiation. Many of the compounds provide highly potent analgesia with immediate onset and a short duration of action. These properties are highly desirable in circumstances where acute severe pain must be eliminated over a short period of time, such as in anesthesiology. The preferred compounds of the present invention have been found to provide reduced rigidity at high doses, superior motor coordination recovery, or less respiratory and/or cardiovascular depressive activity when compared to fentanyl, N-phenyl-N-[1-(2-phenylethyl)-2-piperidinyl]-propanamide.

The compounds of the present invention may be used together with a pharmaceutically acceptable carrier to provide pharmaceutical compositions and can be administered to mammals such as man in amounts sufficient to provide analgesic effects.

As set out above, the analgesic compounds of the present invention have the general formula (I):

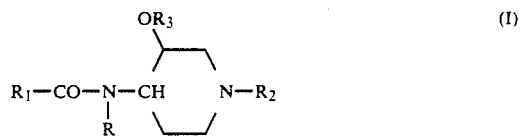

including optically active isomeric forms, cis/trans isomeric forms and the pharmaceutically acceptable acid addition salts thereof, wherein R, $R_1$, $R_2$ and $R_3$ are defined as set forth below.

Group R in Formula (I) above is an aryl group selected from the group consisting of phenyl and substituted phenyl, wherein the substituents on the phenyl group are independently selected from the group consisting of halogen, lower-alkyl, lower-alkoxy, and combinations thereof. The preferred substituents are selected from the group consisting of fluoro and methoxy. The preferred position for attachment of a substituent to the phenyl ring is at the 2 (ortho) position. In a preferred embodiment, the R group is a member selected from the group consisting of phenyl, 2-fluorophenyl and 2-methoxyphenyl.

Group $R_1$ in Formula (I) above is an alkyl group selected form the group consisting of lower-alkyl, lower-alkenyl, and lower-alkoxy lower-alkyl, each alkyl group having from 1 to 6 carbon atoms. In a preferred embodiment, the $R_1$ group is a member selected from the group consisting of methyl, ethyl, methoxymethyl and 1-methoxyethyl.

Group $R_2$ in Formula (I) above is a substituted or unsubstituted ring system selected from the group consisting of phenyl lower-alkyl, monocyclic heterocyclic lower-alkyl ring systems having 5 to 6 ring member atoms and fused bicyclic and tricyclic heterocyclic lower-alkyl ring systems having 5 to 6 ring member atoms in each ring of the polycyclic ring system. The heteroatom may be selected from the group consisting of nitrogen, sulfur and oxygen.

In a preferred embodiment, group $R_2$ in Formula (I) above is a member selected from the group consisting of phenyl lower-alkyl, thienyl lower-alkyl, pyrazolyl lower-alkyl, tetrazolyl lower-alkyl, 4,5-dihydro-5-oxo-1H-tetrazolyl lower-alkyl, 1,3-dihydro-1,3-dioxo-2H-isoindolyl (N-phthalimidyl) lower-alkyl, and 2,3-dihydro-2-oxo-1H-benzimidazolyl lower-alkyl.

In a more preferred embodiment, group $R_2$ in Formula (I) above is a member selected from the group consisting of phenyl lower-alkyl, 2-thienyl lower-alkyl, 3-thienyl lower-alkyl, 1H-pyrazol-1-yl lower-alkyl, 2H-tetrazol-2-yl lower-alkyl, 4,5-dihydro-5-oxo-1H-tetrazol-1-yl lower-alkyl which is substituted in the 4-position with lower-alkyl, 1,3-dihydro-1,3-dioxo-2H-isoindol-2-yl (N-phthalimidyl) lower-alkyl, and 2,3-dihydro-2-oxo-1H-benzimidazolyl lower-alkyl which is substituted in the 3-position with lower-alkyl.

In a most preferred embodiment, group $R_2$ in Formula (I) above is a member selected from the group consisting of phenylmethyl; 2-phenylethyl, 2-(2-thienyl)ethyl, 2-(1H-pyrazol-1-yl)ethyl, 2-(2H-tetrazol-2-yl)ethyl, 2-(4-ethyl-4,5-dihydro-5-oxo-1H-tetrazol-1-yl)ethyl, 2-(1,3-dihydro-1,3-dioxo-2H-isoindol-2-yl)ethyl, and, 2-(3-ethyl-2,3-dihydro-2-oxo-1H-benzimidazol-1-yl)ethyl.

The phenyl or heterocyclic ring may be unsubstituted or substituted, wherein the substituent group is a member independently selected from the group consisting of halogen, lower-alkyl, lower-alkoxy, halogenated lower-alkyl, and combinations thereof. In a preferred embodiment, the substituent group is a member selected from the group consisting of fluoro, chloro, iodo, methyl, ethyl, isopropyl, methoxy, trifluoromethyl, and combinations thereof.

The lower-alkyl group is a member selected from the group consisting of branched or unbranched hydrocarbon groups containing from 1 to 7 carbon atoms. In a preferred embodiment, the lower-alkyl group is a member selected from the group consisting of methyl and ethyl.

Group $R_3$ in Formula (I) above is a member selected from the group consisting of hydrogen, lower-alkyl and lower-alkyl aryl. In a preferred embodiment, the $R_3$ group is a member selected from the group consisting of hydrogen, methyl and phenylmethyl.

The term lower-alkyl groups, as used herein, means branched or unbranched hydrocarbon groups containing from 1 to 7 carbon atoms. The term lower-alkoxy groups, as used herein, means branched or unbranched hydrocarboxy groups containing from 1 to 7 carbon atoms. Preferred heterocyclic groups include from 2 to 12 member atoms and can include the substituents discussed above in connection with heterocyclic groups. The term halogen, as used herein, refers to the chemically related elements consisting of fluorine, chlorine, bromine and iodine.

The compounds of the present invention which have at least one asymmetric carbon atom can exist in optically active isomeric forms. For example, in compounds in which $R_2$ is a 2-phenyl-1-propyl or 1-phenyl-2-propyl group, etc., the carbon adjacent to the piperidinyl nitrogen is an asymmetric carbon atom and such compounds can therefore exist in optical active isomeric (enantiomeric) forms. Such isomeric forms can be isolated from the racemic mixtures by techniques known to those skilled in the art.

The 3-alkoxypiperidine substituted compounds of the present invention exist in cis and trans form. Such compounds can be used as a mixture of such forms but many times one form is more active than the other or one form has other desirable characteristics. Thus many times it is desirable to resolve the cis/trans mixture. This resolution can be accomplished by techniques conventional in the art for such purpose, e.g., chromatographic techniques such as column chromatography or high pressure liquid chromatography or simple recrystallization techniques.

The compounds of the present invention can be prepared by various methods. In general, the desired compounds having Formula (I) above can be prepared by reacting a compound having the formula:

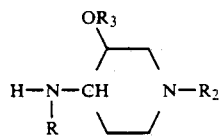

with a compound having the formula:

$R_1$—CO—X or $(R_1CO)_2O$ or by reacting a compound having the formula:

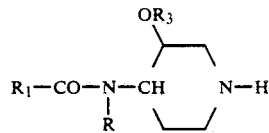

with a compound having the formula:

$R_2X$ wherein the substituent groups R, $R_1$, $R_2$ and $R_3$ have the definitions set out above, and X represents halide or its reactive equivalent. Examples of halide reactive equivalents are toluene sulfonate, phenyl sulfonate, methyl sulfonate and the like.

In the first reaction, when the $R_2$ group is phenylmethyl (benzyl), the phenylmethyl group can be cleaved by hydrogenolysis or by reaction with 1-chloroethyl chloroformate followed by hydrolysis with methanol, see R. A. Olofson et al., *J. Oro. Chem.*. 49, pp. 2081-2082 (1984), and replaced with other $R_2$ groups such as furanyl lower-alkyl, pyrazoyl lower-alkyl and the like. The preparation of secondary amines of the latter type has been described by P. G. H. Van Daele et al., *Arzneim-Forsch. Drug Res.*, 26, p. 1521, (1976).

Several convenient routes for the preparation of the compounds of the invention begin with known piperidone starting materials as shown below:

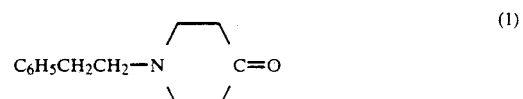

or

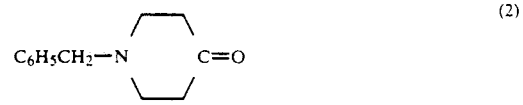

The compound 1-(2-phenylethyl)-4-piperidone (1), can be prepared according to the procedure published by A. H. Becket, A. F. Casey and G. Kirk, *J. Med Pharm. Chem.*, Vol. 1, p. 37 (1959). The compound 1-phenylmethyl-4-piperidone (2), can be prepared in an analogous manner by the procedure described by C. R. Ganellin and R. G. Spickch, *J. Med. Chem.*, Vol. 8, p. 619 (1965) or P. M. Carabateas and L. Grumbach, *J. Med. Pharm. Chem.*, Vol. 5, p. 913 (1962).

In one example of a method for preparing the compounds of the present invention, 1-phenylmethyl-4-piperidone or 1-(2-(phenyl)ethyl)-4-piperidone is reacted with iodobenzene diacetate to form ketal intermediate (3a), see Van Daele et al., *Drug Development Research*, 8, pp. 225–232 (1986) and Moriarty et al., *Tetrahedron Letters*, 25, pp. 4745–4748 (1984). The desired $R_3$ substituent group can then be introduced by reacting intermediate (3a) with an appropriately reactive molecule $R_3$-X, wherein X is halogen, such as chlorine, bromine, or iodine, or its reactive equivalent, to obtain intermediate (4a). Ketal (4a) is then reconverted to the ketone (5a) to provide the desired starting material.

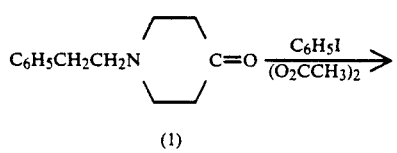

(1)

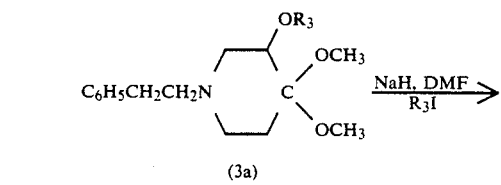

(3a)

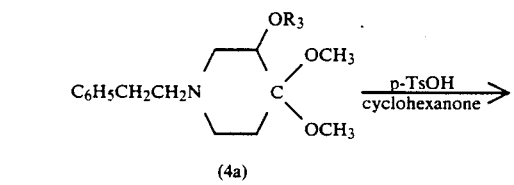

(4a)

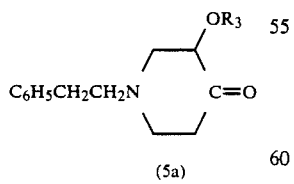

(5a)

1-(2-(Phenyl)ethyl)-3-substituted-4-piperidine (5a) is reacted with an unsubstituted or substituted amine to form a Schiff base (6a). The Schiff base is then reduced, for example, with sodium borohydride to yield the unsubstituted or substituted 1-phenylmethyl or 1-(2-(phenyl)ethyl)-3-substituted-4-aminopiperidine compound. See for example, S. Grossman et al., *Arch. Pharm.* (Weinheim) 311, p. 1010 (1978). The following reaction scheme, wherein R in the compound $RNH_2$ is according to the definition of the present invention, illustrates such a method:

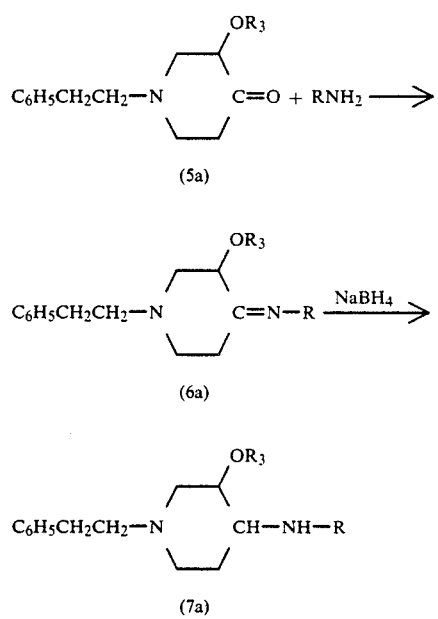

(5a)

(6a)

(7a)

Amine compound (7a) can be reacted with an appropriate acid halide (e.g., $R_1COCl$) or an anhydride (e.g., $(R_1CO)_2O$) to introduce the desired $R_1$-carbonyl group on the nitrogen atom and thereby obtain compound (I) of the present invention, according to the reaction scheme shown below:

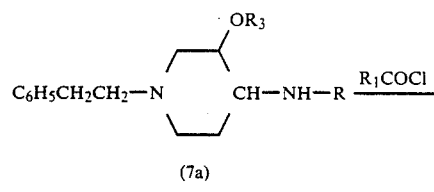

(7a)

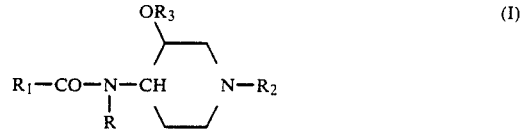

(I)

The cis and trans isomers of compound (7a) can be separated before or after reaction with an acid halide or anhydride, as set out above, thereby obtaining cis and trans isomers of compound (I) of the present invention. The separation of the cis/trans isomers can be carried out according to the following reaction scheme:

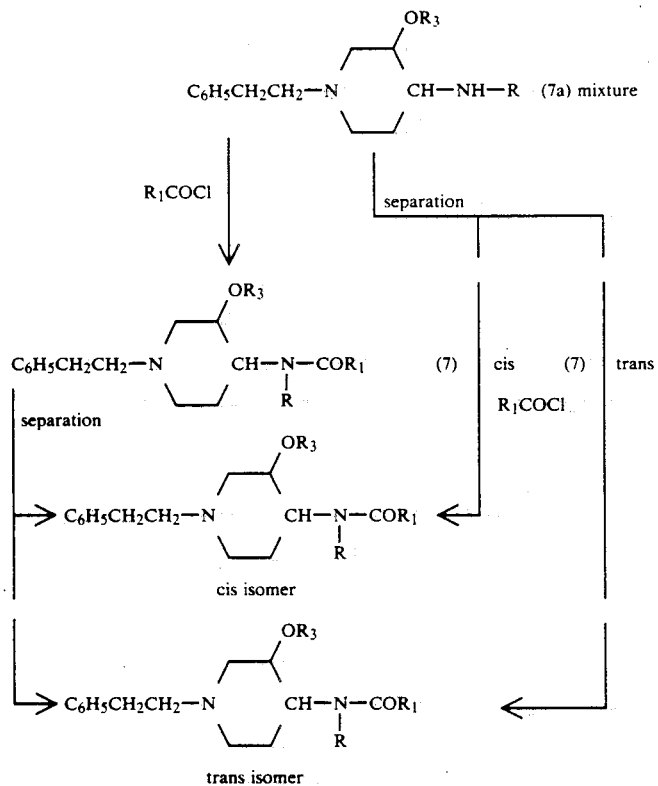

When the desired $R_2$ substituent group is not phenylethyl, one procedure for preparing compounds of the present invention with different $R_2$ groups is to remove the phenylmethyl group in compound (2), after oxidation of the ketone to the corresponding (5b) type compound, by hydrogenolysis (for example, using hydrogen over 10% palladium on carbon) or by reaction with 1-chloroethyl chloroformate above and replace it with a desired $R_2$ group. For example, compounds of the invention can be prepared according to the following scheme:

As set out above, the cis and trans isomers of compound (7b) can be separated prior to the next step. After any such cis/trans separation, compound (7b) can be reacted with an appropriate acid halide (e.g., $R_1COCl$) or an anhydride (e.g., $(R_1CO)_2O$) to introduce the desired $R_1$-carbonyl group on the nitrogen atom and thereby obtain compound (I) of the present invention. Compound (I) can then be reacted with hydrogen over palladium on carbon or with 1-chloroethyl chloroformate according to the following reaction scheme to remove the phenylmethyl group and prepare piperidinyl intermediate (8):

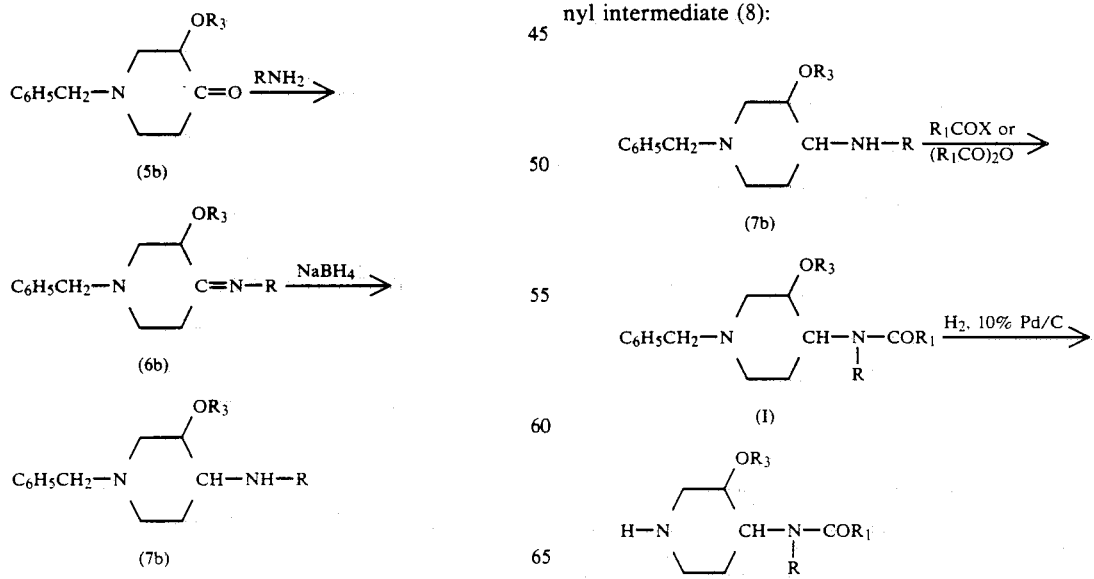

The desired $R_2$ substituent group can then be introduced by reacting compound (8) with an appropriately reactive molecule $R_2$-X, wherein X is halogen, such as chlorine, bromine, or iodine, or its reactive equivalent, to obtain compound (I) of the present invention according to the reaction scheme illustrated below:

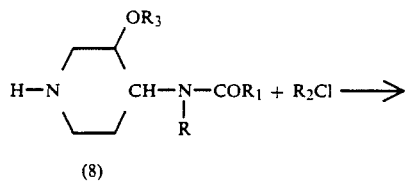
(8)

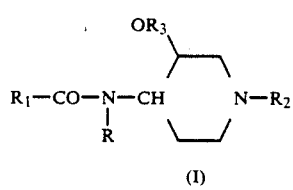
(I)

The reaction of $R_2$-X with a piperidinyl intermediate such as compound (8) can be conducted in an inert organic solvent such as, for example, an aromatic hydrocarbon, a ketone such as 4-methyl-2-pentanone and the like, an ether such as 1,4-dioxane, diethylether, tetrahydofuran, 1,2-dimethoxyethane and the like, or N,N-dimethylformamide or acetonitrile. The addition of an appropriate base, such as an alkali metal carbonate, may be utilized to neutralize the acid generated during the reaction. The addition of an iodide salt, such as an alkali metal iodide, may be appropriate. The temperature of the reaction mixture may be raised to increase the rate of reaction when appropriate.

In an alternative procedure, the phenylmethyl group can first be removed by hydrogenolysis or by reaction with 1-chloroethyl chloroformate prior to separation of the cis/trans isomers of compound (7) to obtain compound (I) of the present invention with the $R_1$ and $R_2$ groups introduced according to one of the two schemes shown below:

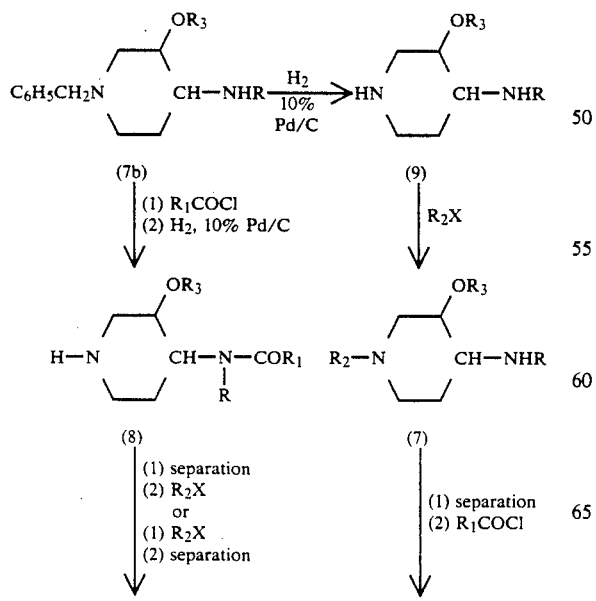

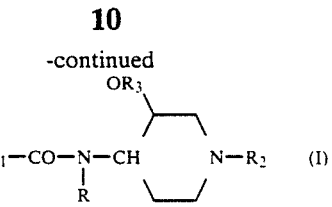
cis iosmer

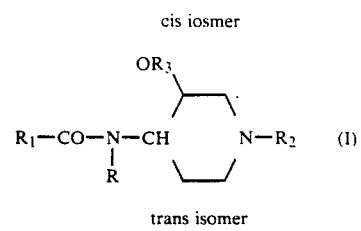
trans isomer

In a second example of a method for preparing the compounds of the present invention, an intermediate such as 1-(2-(phenyl)ethyl)-4-piperidineamine (10) is utilized. In this method, the primary amine is reacted with a desired group RX, where X is a halide or its reactive equivalent, to form a secondary amine precursor of type (7). The secondary amine is then acylated with an appropriate acid halide (e.g., $R_1$COCl) or an anhydride (e.g., $(R_1CO)_2O$) to introduce the desired $R_1$-carbonyl group on the nitrogen atom. See, for example, Y. Zhu et al., *Acta Pharm. Sinica*, 16, p. 199 (1981). The following reaction scheme, wherein R and $R_1$ are groups within the definition of the present invention, illustrates such a method to make compound (I) of the present invention.

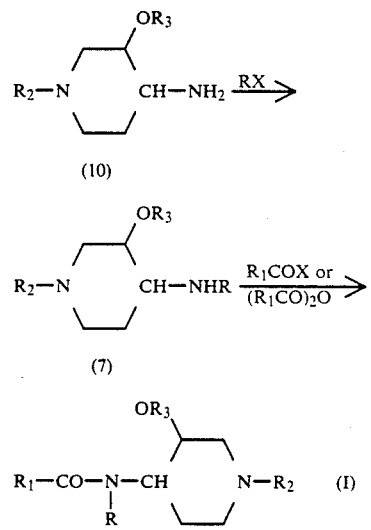

In a third example of a method for preparing the compounds of the present invention, the same intermediate, such as 1-(2-(phenyl)ethyl)-4-piperidineamine (10), is utilized. In this method, the primary amine is reacted with an oxo-derivative of the group R to form a secondary amine precursor. The oxo-intermediate is reduced prior to acylation. See, for example, Langhein et al., *Offenlegungschrift*, 234, p. 1965 (1975); *Chem. Abstr.* 82, 156121w (1975).

The compounds of the present invention while effective in the form of the free base may be formulated and administered in the form of the therapeutically or pharmaceutically acceptable acid addition salts for purposes of stability, convenience of crystallization, increased solubility and the like. These acid addition salts include inorganic acid salts such as hydrochloric, hydrobromic, sulfuric, nitric, phosphoric, perchloric acid salts and the like; and organic acid salts such as acetic, trifluoroacetic, propionic, oxalic, hydroxyacetic, methoxyacetic, 2-hydroxypropanoic, 2-oxopropanoic, propanedioic, 2-hydroxy-butanedioic, benzoic, 2-hydroxybenzoic, 4-amino-2-hydroxy-benzoic, 3-phenyl-2-propenoic, alpha-hydroxybenzeneacetic, methanesulfonic, ethanesulfonic, benzenesulfonic, toluene-sulfonic, cyclohexanesulfamic, succinic, tartaric, citric, maleic, fumaric acid salts and the like. The preferred acid addition salts are chloride, oxalate and citrate. These acid addition salts can be prepared by conventional methods, such as by treatment of the free base of the inventive compound with the appropriate acid.

The compounds of the present invention, prepared in the free base form, can be combined with a pharmaceutically acceptable carrier to provide a pharmaceutical composition. Suitable carriers for the free bases include propylene glycol-alcohol-water, isotonic water, sterile water for injection (USP), emulphor TM -alcohol-water, cremophor-EL TM or other suitable carriers known to those skilled in the art.

The compounds of the present invention, prepared in the pharmaceutically acceptable acid addition salt form, can also be combined with a pharmaceutically acceptable carrier to provide a pharmaceutical composition. Suitable carriers for the acid addition salts include isotonic water, sterile water for injection (USP), alone or in combination with other solubilizing agents such as ethanol, propylene glycol, or other conventional solubilizing agents known to those skilled in the art.

Of course, the type of carrier will vary depending upon the mode of administration desired for the pharmaceutical composition as is conventional in the art. A preferred carrier is an isotonic aqueous solution of the inventive compound.

The compounds of the present invention can be administered to mammals, e.g., animals or humans, in amounts effective to provide the desired analgesic therapeutic effect or to reverse the actions of an opiate analgesic. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can be as low as about 0.00005 mg/kg, which the practitioner may titrate to the desired effect.

The compounds of the present invention can be administered parenterally, in the form of sterile solutions or suspensions, such as intravenously, intramuscularly or subcutaneously in the carriers previously described. The compounds may also be administered orally, in the form of pills, tablets, capsules, troches, and the like, as well as sublingually, rectally, or transcutaneously with a suitable pharmaceutically acceptable carrier for that particular mode of administration as is conventional in the art.

For parental therapeutic administration, the compounds of the present invention may be incorporated into a sterile solution or suspension. These preparations should contain at least about 0.1% of the inventive compound, by weight, but this amount may be varied to between about 0.1% and about 50% of the inventive compound, by weight of the parental composition. The exact amount of the inventive compound present in such compositions is such that a suitable dosage level will be obtained. Preferred compositions and preparations according to the present invention are prepared so that a paranteral dosage unit contains from between about 0.5 to about 100 milligrams of the inventive compound.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parental preparations may be enclosed in ampules, disposable syringes, or multiple dose vials made of glass or plastic.

The compounds of the present invention can also be administered orally. For oral therapeutic administration, the compounds may be incorporated with excipients and used in the form of tablets, capsules, elixirs, suspensions, syrups, wafers, chewing gums and the like. These preparations should contain at least about 4% of the inventive compound, by weight, but this amount may be varied depending upon the particular dosage form from between about 4% to about 70% of the inventive compound, by weight of the oral composition. The exact amount of the compound present in the composition is such that a suitable dosage will be obtained. Preferred compositions and preparations according to the present invention are prepared so that an oral dosage unit form contains from between about 5 to about 300 milligrams of the inventive compound.

The tablets, pills, capsules, troches and the like may also contain the following adjuvants: a binder, such as microcrystalline cellulose gum tragacanth or gelatine; an excipient, such as starch or lactose; a disintegrating agent, such as alginic acid, Primogel, corn starch and the like; a lubricating agent, such as magnesium stearate or Sterotex; a gliding agent, such as colloidal silicon dioxide; a sweetening agent, such as sucrose or saccharin; and a flavoring agent, such as peppermint, methyl salicylate or orange flavoring. When the dosage form is a capsule, it may additionally contain a liquid carrier such as a fatty oil. Other dosage unit forms may contain other materials which modify the physical form of the dosage unit, such as enteric coatings. Thus tablets or pills may be coated with sugar, shellac, or other enteric coating agents. A syrup may contain, in addition to the above adjuvants, sucrose as a sweetening agent, preservatives, dyes, coloring agents and flavoring agents.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is further illustrated by the following examples which are presented for purposes of demonstrating, but not limiting, the preparation of the compounds and compositions of this invention. Related methods for preparing compounds of the type of the present invention are disclosed in U.S. Pat. No. 4,584,303, which disclosure is incorporated herein by reference.

EXAMPLE 1

This Example illustrates the preparation of the intermediate 1-phenylmethyl-3-hydroxy-4,4-dimethoxypiperidine (3b).

1-Phenylmethyl-4-piperidone (18.92g, 100 mmol) in 40 ml of methanol was added slowly over a period of 15 minutes to a solution of potassium hydroxide (16.83g, 100 mmol) in 150 ml of methanol at 0° C. Iodobenzene diacetate (35.43 g, 110 mmol) was then added to the mixture in portions over a period of thirty minutes. The reaction mixture was stirred at room temperature overnight. The mixture was then concentrated under vacuum to remove the excess of methanol and the crude residue was diluted with a mixture of water (500 ml) and dichloromethane (300 ml). The dichloromethane layer was separated and the aqueous phase was again extracted with 150ml of dichloromethane. The combined organic layers were dried over sodium sulfate and concentrated under vacuum. The crude residue was dissolved in 100 ml of hexane and crystallized. The solid was washed with 30ml of hexane to yield the intermediate 1-phenylmethyl-3-hydroxy-4,4-dimethoxypiperidine (3b, 6.48 g, 25.8%).

EXAMPLE 2

This Example illustrates the preparation of the intermediate 1-phenylmethyl-3-methoxy-4,4-dimethoxypiperidine (4b).

1-Phenylmethyl-3-hydroxy-4,4-dimethoxypiperidine (3b, 5.5 g, 22 mmol) from Example 1 in 30 ml of dimethylformamide was added slowly to a stirred suspension of sodium hydride (0.81 g, 27 mmol, 80% oil suspension) in 100 ml of dimethylformamide. The reaction mixture was warmed to 60° C. for 2 hours, then cooled to 0° C. whereupon methyl iodide (3.8 g, 27 mmol) was slowly added to the mixture. The reaction mixture was stirred overnight at room temperature then quenched with 10 ml of 10% sodium hydroxide solution. The reaction mixture was concentrated under vacuum, the residue slurried in 300 ml of water and the aqueous mixture extracted with 3×100 ml of ether. The combined organic layers were dried over magnesium sulfate, concentrated under vacuum, then purified by column chromatography (alumina; ethyl acetate/hexane; 2.5:1) to yield the intermediate 1-phenylmethyl-3-methoxy-4,4-dimethoxypiperidine (4b, 3.77 g, 64.6%, $R_f$ 0.63).

EXAMPLE 3

This Example illustrates the preparation of the intermediate 1-phenylmethyl-3-methoxy-4-piperidone (5b).

1-phenylmethyl-3-methoxy-4,4-dimethoxypiperidine (4b, 2.22g, 8.36 mmol) from Example 2 and p-toluenesulfonic acid (3.15 g, 16.6 mmol) was heated to reflux in acetone (100ml) for three hours. After being cooled, the reaction solution was concentrated under vacuum, then slurried in 40ml of 10% sodium hydroxide solution. The aqueous mixture was extracted with 2×60 ml of ether, the combined organic layers were dried over magnesium sulfate, then concentrated under vacuum. The crude residue was purified by chromatography (silica gel; ethyl acetate/hexane; 1:1) to provide the intermediate 1-phenylmethyl-3-methoxy-4-piperidone (5b, 1.66 g, 90%).

EXAMPLE 4

This Example illustrates the preparation of the intermediate 1-phenylmethyl-3-methoxy-4-phenylaminopiperidine (7b).

Sodium cyanoborohydride (0.17 g, 27 mmol) and 5.2 g of 3A molecular sieves were slowly added at room temperature to a stirred solution of 1-phenylmethyl-3-methoxy-4-piperidone (5b, 1 g, 4.56 mmol) from Example 3 in 40 ml of methanol, 2.55 g (27 mmol) of aniline and 3.57 ml of 2.55N hydrochloric acid in methanol. The reaction mixture was stirred at room temperature for 3 days, after which time the molecular sieves were filtered off and the solution was made acidic with 10ml of 10% hydrochloric acid. The methanol was evaporated under vacuum and the residue was diluted with 20 ml of water, then extracted with ether (50 ml). The aqueous layer was then made alkaline with 10% sodium hydroxide ( solution and extracted with 3×100 ml of ether. The combined organic layers were dried, then concentrated under vacuum and purified by column chromatography (silica gel; ethyl acetate/hexane; 1:1) to yield the intermediates cis-1-phenylmethyl-3-methoxy-4-phenylaminopiperidine (7b, 0.52 g, 38.23%) and trans-1-phenylmethyl-3-methoxy-4-phenylaminopiperidine (7b, 0.05 g, 3.7%).

EXAMPLE 5

This Example illustrates the preparation of a compound of the present invention cis-N-phenyl-N-(1-phenylmethyl-3-methoxy-4-piperidinyl)propanamide (I).

Propionyl chloride (0.77 g, 8.3 mmol) was added to cis-1-phenylmethyl-3-methoxy-4-phenylaminopiperidine (7b, 1.6 g, 5.3 mmol) from Example 4 in 30 ml of dichloromethane. The reaction solution was stirred at room temperature overnight and subsequently diluted with 20ml of 10% sodium hydroxide solution. The organic layer was separated and the aqueous layer was extracted with 2×50 ml of dichloromethane. The combined organic layers were dried and concentrated under vacuum to yield 1.84 g (99%) of crude cis-N-phenyl-N-(1-phenylmethyl-3-methoxy-4-piperidinyl)propanamide (I).

EXAMPLE 6

This Example illustrates the preparation of the intermediate cis-N-phenyl-N-(3-methoxy-4-piperidinyl)-propanamide (8) for the preparation of compounds having different $R_2$ substituent groups.

cis-N-Phenyl-N-(1-phenylmethyl-3-methoxy-4piperidinyl)propanamide (I, 1.84 g, 5.22 mmol) from Example 5 was hydrogenated in 300 ml of methanol using 0.5 mg of Pd(OH) as catalyst over a period of 4 hours. After the usual work-up, a quantitative yield of crude intermediate cis-N-phenyl-N-(3-methoxy-4-piperidinyl)-propanamide (8) was obtained.

EXAMPLE 7

This Example illustrates the preparation of another compound of the present invention cis-N-phenyl-N-(1-phenylethyl-3-methoxy-4-piperidinyl)propanamide (I).

cis-N-Phenyl-N-(3-methoxy-4-piperidinyl)propanamide (8, 0.5 g, 1.9 mmol) from Example 6, phenylethyl bromide (0.40 g, 2.2 mmol) and 2.76 g (19 mmol) of potassium carbonate in 100 ml of acetonitrile were heated to reflux overnight. The reaction solution was concentrated under vacuum and the crude residue was purified by chromatography (silica gel; ethyl acetate) to yield 0.43 g (62%, $R_f$ 0.326) of pure cis-N-phenyl-N-(1-phenylethyl-3-methoxy-4-piperidinyl)propanamide (I).

EXAMPLES 8–38

Further examples of compounds within the scope of the present invention which may be prepared by procedures analogous to those described above include:

cis-N-(phenyl)-N-[1-(2-(2H-tetrazol-2-yl)ethyl)-3-methoxy-4-piperidinyl]propanamide cis-N-(phenyl)-N-[1-(2-(1,3-dihydro-1,3-dioxo-2H-isoindol-2-yl)ethyl)-3-methoxy-4-piperidinyl]methoxyacetamide cis-N-(phenyl)-N-[1-(2-(phenyl)ethyl)-3-methoxy-4-piperidinyl]propanamide cis-N-(phenyl)-N-[1-(2-(4-ethyl-4,5-dihydro-5-oxo-1H-tetrazol-1-yl)ethyl)-3-methoxy-4-piperidinyl]propanamide cis-N-(phenyl)-N-[1-(2-(1,3-dihydro-1,3-dioxo-2H-isoindol-2-yl)ethyl)-3-methoxy-4-piperidinyl]propanamide cis-N-(2-fluorophenyl)-N-[1-(2-(phenyl)ethyl)-3-methoxy-4-piperidinyl]methoxyacetamide cis-N-(2-fluorophenyl)-N-[1-(2-(1,3-dihydro-1,3-dioxo-2H-isoindol-2-yl)ethyl)-3-methoxy-4piperidinyl]methoxyacetamide cis-N-(2-fluorophenyl)-N-[1-(2-(2H-tetrazol-2-yl)-ethyl)-3-methoxy-4-piperidinyl]methoxyacetamide cis-N-(2-fluorophenyl)-N-[1-(2-(4-ethyl-4,5-dihydro-5-oxo-1H-tetrazol-1-yl)ethyl)-3-methoxy-4-piperidinyl]methoxyacetamide cis-N-(2-fluorophenyl)-N-[1-(2-(2-thienyl)ethyl)-3-methoxy-4-piperidinyl]methoxyacetamide cis-N-(2-fluorophenyl)-N-[1-(2-(1,3-dihydro-1,3-dioxo-2H-isoindol-2-yl)ethyl)-3-methoxy-4-piperidinyl]propanamide    cis-N-(2-fluorophenyl)-N-[1-(2-(1,3-dihydro-1,3-dioxo-2H-isoindol-2-yl)ethyl)-3-methoxy-4-piperidinyl]propanamide cis-N-(2-fluorophenyl)-N-[1-(2-(4-ethyl-4,5-dihydro-5-oxo-1H-tetrazol-1-yl)ethyl)-3-methoxy-4-piperidinyl]propanamide trans-N-(2-fluorophenyl)-N-[1-(2-(4-ethyl-4,5-dihydro-5-oxo-1H-tetrazol-1-yl)ethyl)-3-methoxy-4-piperidinyl]methoxyacetamide trans-N-(2-fluorophenyl)-N-[1-(2-(4-ethyl-4,5-dihydro-5-oxo-1H-tetrazol-1-yl)ethyl)-3-methoxy-4-piperidinyl]propanamide cis-N-(2-fluorophenyl)-N-[1-(2-(phenyl)ethyl)-3-methoxy-4-piperidinyl]propanamide trans-N-(2-fluorophenyl)-N-[1-(2-(phenyl)ethyl)-3-methoxy-4-piperidinyl]methoxyacetamide cis-N-(2-fluorophenyl)-N-[1-(2-(2-thienyl)ethyl)-3-methoxy-4-piperidinyl]propanamide trans-N-(2-fluorophenyl)-N-[1-(2-(2-thienyl)ethyl)-3-methoxy-4-piperidinyl]methoxyacetamide cis-N-(phenyl)-N-[1-(phenylmethyl)-3-methoxy-4-piperidinyl]methoxyacetamide cis-N-(phenyl)-N-[1-(2-(3-ethyl-2,3-dihydro-2-oxo-1H-benzimidazol-1-yl)ethyl)-3-methoxy-4-piperidinyl]methoxyacetamide trans-N-(2-fluorophenyl)-N-[1-(2-(1,3-dihydro1,3-dioxo-2H-isoindol-2-yl)ethyl)-3-methoxy-4-piperidinyl]propanamide trans-N-(2-fluorophenyl)-N-[1-(2-(2-thienyl)ethyl)-3-methoxy-4-piperidinyl]propanamide trans-N-(2-fluorophenyl)-N-[1-(2-(phenyl)ethyl)-3-methoxy-4-piperidinyl]propanamide trans-N-(phenyl)-N-[1-(2-(1,3-dihydro-1,3-dioxo-2H-isoindol-2-yl)ethyl)-3-methoxy-4-piperidinyl]propanamide cis-N-(phenyl)-N-[1-(2-(4-ethyl-4,5-dihydro-5-oxo-1H-tetrazol-1-yl)ethyl)-3-methoxy-4-piperidinyl]methoxyacetamide cis-N-(phenyl)-N-[1-(2-(phenyl)ethyl)-3-methoxy-4-piperidinyl]methoxyacetamide cis-N-(phenyl)-N-[1-(2-(phenyl)ethyl)-3-methoxy-4-piperidinyl]propanamide cis-N-(2-fluorophenyl)-N-[1-(phenylmethyl)-3-phenylmethoxy-4-piperidinyl]methoxyacetamide cis-N-(2-fluorophenyl)-N-[1-(2-(phenyl)ethyl)-3-phenylmethoxy-4-piperidinyl]methoxyacetamide cis-N-(2-fluorophenyl)-N-[1-(2-(phenyl)ethyl)-3-hydroxy-4-piperidinyl]propanamide

EXAMPLE 39

A pharmaceutical composition for parental or intravenous analgesic administration can be prepared from the following ingredients:

| COMPONENTS | AMOUNTS |
| --- | --- |
| cis-N-(phenyl)-N-[1-(2-(2H-tetrazol-2-yl)-ethyl)-3-methoxy-4-piperidinyl]-propanamide | 1 mg |
| isotonic water | 10 liters |

Of course, other compounds of this invention such as those set out in Examples 8–38 may be substituted for cis-N-(phenyl)-N-[1-(2-(2H-tetrazol-2-yl)-ethyl)-3-methoxy-4-piperidinyl]propanamide with the relative amount of such other compounds in the compositions depending upon their analgesic activity.

EXAMPLE 40

A number of compounds in accordance with the present invention were tested for their analgesic properties. Specifically, the acid addition salts of the compounds, tested in accordance with the invention, were dissolved in sterile water for injection, USP, to form a solution, the concentration of which may vary from 0.00001 mg/ml to 5 mg/ml. The solution was administered intraveneously into a mouse tail vain. The $ED_{50}$ values were obtained from the mouse hot plate analgesia test (58° C.) as described in Domer, Floyd R., Animal Experiments in Pharmacological Analysis, Charles C. Thomas, Springfield, 1971, p. 283. The compounds listed in Table 1 were tested by this procedure and found to have the activities listed in the columns on the right side of Table 1.

TABLE 1

| COMPOUNDS | M.P. °C. (oxalate salt) | Ed₅₀ Mg/Kg |
|---|---|---|
| 1. cis-N-(phenyl)-N-[1-(2-(2H-tetrazol-2-yl)-ethyl)-3-methoxy-4-piperidinyl]propanamide | 174–176 | 2.2 |
| 2. cis-N-(phenyl)-N-[1-(2-(1,3-dihydro-1,3-dioxo-2H-isoindol-2-yl)ethyl)-3-methoxy-4-piperidinyl]methoxyacetamide | 95–96 | I* |
| 3. cis-N-(phenyl)-N-[1-(2-(phenyl)ethyl)-3-methoxy-4-piperidinyl]propanamide | 183–184 | 0.00064 |
| 4. cis-N-(phenyl)-N-[1-(2-(4-ethyl-4,5-dihydro-5-oxo-1H-tetrazol-1-yl)ethyl)-3-methoxy-4-piperidinyl]propanamide | 163–165 | 0.384 |
| 5. cis-N-(phenyl)-N-[1-(2-(1,3-dihydro-1,3-dioxo-2H-isoindol-2-yl)ethyl)-3-methoxy-4-piperidinyl]propanamide | 184–185 | 0.768 |
| 6. cis-N-(2-fluorophenyl)-N-[1-(2-(phenyl)ethyl)-3-methoxy-4-piperidinyl]methoxyacetamide | 184–185 | 0.000641 |
| 7. cis-N-(2-fluorophenyl)-N-[1-(2-(1,3-dihydro-1,3-dioxo-2H-isoindol-2-yl)ethyl)-3-methoxy-4-piperidinyl]methoxyacetamide | 126–128 | I |
| 8. cis-N-(2-fluorophenyl)-N-[1-(2-(2H-tetrazol-2-yl)-ethyl)-3-methoxy-4-piperidinyl]methoxyacetamide | 144–145 | I |
| 9. cis-N-(2-fluorophenyl)-N-[1-(2-(4-ethyl-4,5-dihydro-5-oxo-1H-tetrazol-1-yl)ethyl)-3-methoxy-4-piperidinyl]methoxyacetamide | 93–95 | 0.554 |
| 10. cis-N-(2-fluorophenyl)-N-[1-(2-(2-thienyl)-ethyl)-3-methoxy-4-piperidinyl]methoxyacetamide | 186–187 | 0.00046 |
| 11. cis-N-(2-fluorophenyl)-N-[1-(2-(1,3-dihydro-1,3-dioxo-2H-isoindol-2-yl)ethyl)-3-methoxy-4-piperidinyl]propanamide | 112–114 | 0.489 |
| 12. cis-N-(2-fluorophenyl)-N-[1-(2-(1,3-dihydro-1,3-dioxo-2H-isoindol-2-yl)ethyl)-3-methoxy-4-piperidinyl]propanamide | 96–98 | I |
| 13. cis-N-(2-fluorophenyl)-N-[1-(2-(4-ethyl-4,5-dihydro-5-oxo-1H-tetrazol-1-yl)ethyl)-3-methoxy-4-piperidinyl]propanamide | 144–146 | 0.124 |
| 14. trans-N-(2-fluorophenyl)-N-[1-(2-(4-ethyl-4,5-dihydro-5-oxo-1H-tetrazol-1-yl)ethyl)-3-methoxy-4-piperidinyl]methoxyacetamide | 150–152 | I |
| 15. trans-N-(2-fluorophenyl)-N-[1-(2-(4-ethyl-4,5-dihydro-5-oxo-1H-tetrazol-1-yl)ethyl)-3-methoxy-4-piperidinyl]propanamide | 139–141 | I |
| 16. cis-N-(2-fluorophenyl)-N-[1-(2-(phenyl)ethyl)-3-methoxy-4-piperidinyl]propanamide | 195–197 | 0.00091 |
| 17. trans-N-(2-fluorophenyl)-N-[1-(2-(phenyl)-ethyl)-3-methoxy-4-piperidinyl]methoxyacetamide | 144–145 | 0.047 |
| 18. cis-N-(2-fluorophenyl)-N-[1-(2-(2-thienyl)-ethyl)-3-methoxy-4-piperidinyl]propanamide | 183–185 | 0.0013 |
| 19. trans-N-(2-fluorophenyl)-N-[1-(2-(2-thienyl)-ethyl)-3-methoxy-4-piperidinyl]methoxyacetamide | 134–135 | 0.015 |
| 20. cis-N-(phenyl)-N-[1-(phenylmethyl)-3-methoxy-4-piperidinyl]methoxyacetamide | 126–127 | I |
| 21. cis-N-(phenyl)-N-[1-(2-(3-ethyl-2,3-dihydro-2-oxo-1H-benzimidazol-1-yl)ethyl)-3-methoxy-4-piperidinyl]methoxyacetamide | 118–119 | 0.538 |
| 22. trans-N-(2-fluorophenyl)-N-[1-(2-(1,3-dihydro-1,3-dioxo-2H-isoindol-2-yl)ethyl)-3-methoxy-4-piperidinyl]propanamide | 126–128 | 0.913 |
| 23. trans-N-(2-fluorophenyl)-N-[1-(2-(2-thienyl)-ethyl)-3-methoxy-4-piperidinyl]propanamide | 155–157 | 0.01 |
| 24. trans-N-(2-fluorophenyl)-N-[1-(2-(phenyl)-ethyl)-3-methoxy-4-piperidinyl]propanamide | 170–173 | 0.0019 |
| 25. trans-N-(phenyl)-N-[1-(2-(1,3-dihydro-1,3-dioxo-2H-isoindol-2-yl)ethyl)-3-methoxy-4-piperidinyl]propanamide | 124–126 | I |
| 26. cis-N-(phenyl)-N-[1-(2-(4-ethyl-4,5-dihydro-5-oxo-1H-tetrazol-1-yl)ethyl)-3-methoxy-4-piperidinyl]methoxyacetamide | 158–160 | I |
| 27. cis-N-(phenyl)-N-[1-(2-(phenyl)ethyl)-3-methoxy-4-piperidinyl]methoxyacetamide | 165–167 | 0.0027 |
| 28. cis-N-(phenyl)-N-[1-(2-(phenyl)ethyl)-3-methoxy-4-piperidinyl]propanamide | 153–154 | 0.525 |
| 29. cis-N-(2-fluorophenyl)-N-[1-(phenylmethyl)-3-phenylmethoxy-4-piperidinyl]methoxyacetamide | 156–158 | I |
| 30. cis-N-(2-fluorophenyl)-N-[1-(2-(phenyl)ethyl)-3-phenylmethoxy-4-piperidinyl]methoxyacetamide | 171–172 | 0.724 |
| 31. cis-N-(2-fluorophenyl)-N-[1-(2-(phenyl)ethyl)- | 153–154 | 0.525 |

| COMPOUNDS | M.P. °C. (oxalate salt) | Ed₅₀ Mg/Kg |
|---|---|---|
| 3-hydroxy-4-piperidinyl]propanamide | | |

*Inactive

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A compound having the formula:

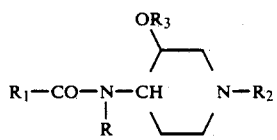 (I)

an optically active isomeric form thereof, a, cis/trans isomeric form thereof or a pharmaceutically acceptable acid addition salt thereof, wherein:

R is an aryl group selected from the group consisting of phenyl and substituted phenyl, wherein the substituents on the phenyl group are selected from the group consisting of halogen, lower-alkyl, lower alkoxy, and combinations thereof;

$R_1$ is selected from the group consisting of lower-alkyl, lower-alkenyl, and lower-alkoxy lower alkyl, each alkyl group having from 1 to 6 carbon atoms;

$R_2$ is thienyl lower-alkyl and $R_3$ is selected from the group consisting of hydrogen, lower-alkyl and lower-alkyl aryl.

2. A compound according to claim 1, wherein R is selected from the group consisting of phenyl, 2-fluorophenyl and 2-methoxyphenyl.

3. A compound according to claim 1, wherein $R_1$ is selected from the group consisting of methyl, ethyl, methoxymethyl and 1/methoxyethyl.

4. A compound according to claim 1, wherein $R_2$ is 2-thienyl lower-alkyl or 3-thienyl lower-alkyl.

5. A compound according to claim 4, wherein $R_2$ is 2-(2-thienyl)ethyl.

6. A compound according to claim 1, wherein $R_3$ is selected from the group consisting of hydrogen, methyl.

7. A compound according to claim 1, which is cis-N-(2-fluorophenyl)-N-[1-(2-(2-thienyl)-ethyl)-3-methoxy-4-piperidinyl]methoxyacetamide, or a pharmaceutically acceptable addition salt thereof.

8. A narcotic analgesic composition comprising a non-toxic pharmaceutically acceptable carrier and an analgesically effective amount of a compound having the formula:

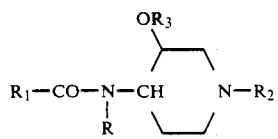 (I)

an optically active isomeric form thereof, a, cis/trans isomeric form thereof or a pharmaceutically acceptable acid addition salt thereof, wherein:

R is an aryl group selected from the group consisting of phenyl and substituted phenyl, wherein the substituents on the phenyl group are selected from the group consisting of halogen, lower-alkyl, lower-alkoxy, and combinations thereof;

$R_1$ is selected from the group consisting of lower-alkyl, lower-alkenyl, and lower-alkoxy lower-alkyl, each alkyl group having from 1 to 6 carbon atoms;

$R_2$ is thienyl lower-alkyl; and $R_3$ is selected from the group consisting of hydrogen, lower-alkyl and lower-alkyl aryl.

9. A composition according to claim 8, wherein R is a member selected from the group consisting of phenyl, 2-fluorophenyl and 2-methoxyphenyl.

10. A composition according to claim 8, wherein $R_1$ is selected from the group consisting of methyl, ethyl, methoxymethyl and 1/methoxyethyl.

11. A composition according to claim 8, wherein $R_2$ is 2-thienyl lower-alkyl or 3-thienyl lower-alkyl.

12. $R_2$ is 2-(2-thienyl)ethyl.

13. A composition according to claim 8, wherein $R_3$ is selected from the group consisting of hydrogen, methyl.

14. A composition according to claim 8, wherein said compound is cis-N-(2-fluorophenyl)-N-[1-(2-(2-thienyl)-ethyl-3-methoxy-4-piperidinyl]-methoxyacetamide or a pharmaceutically acceptable addition salt thereof.

15. A method of producing analgesia in a mammal comprising administering to the mammal in need thereof an analgesically effective amount of a compound having the formula:

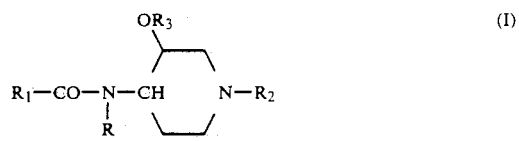 (I)

an optically active isomeric form thereof, a, cis/trans isomeric form thereof or a pharmaceutically acceptable acid addition salt thereof, wherein:

R is an aryl group selected from the group consisting of phenyl and substituted phenyl, wherein the substituents on the phenyl group are selected from the group consisting of halogen, lower-alkyl, lower-alkoxy, and combinations thereof;

$R_1$ is selected from the group, consisting of lower-alkyl, lower-alkenyl, and lower-alkoxy lower-alkyl, each alkyl group having from 1 to 6 carbon atoms;

$R_2$ is thienyl lower-alkyl; and $R_3$ is selected from the group consisting of hydrogen, lower-alkyl and lower-alkyl aryl.

16. A method according to claim 15, wherein R is selected from the group consisting of phenyl, 2-fluorophenyl and 2-methoxyphenyl.

17. A method according to claim 15, wherein $R_1$ is selected from the group consisting of methyl, ethyl, methoxymethyl and 1/methoxyethyl.

18. A method according to claim 15, wherein $R_2$ is 2-thienyl lower-alkyl or 3-thienyl lower-alkyl.

19. A method according to claim 18, wherein $R_2$ is 2-(2-thienyl)ethyl.

20. A method according to claim 15, wherein $R_3$ is selected from the group consisting of hydrogen, methyl.

21. A method according to claim 15, wherein said compound is cis-N-(2-fluorophenyl)-N-[1-(2-(2-thienyl)-ethyl)-3-methoxy-4-piperidinyl]-methoxy-acetamide or a pharmaceutically acceptable addition salt thereof.

* * * * *